(12) United States Patent
Anderson et al.

(10) Patent No.: US 6,303,843 B1
(45) Date of Patent: Oct. 16, 2001

(54) METHOD FOR REMOVING SULFOLANE PRESENT IN HYDROCARBON

(75) Inventors: Richard L. Anderson; Bruce B. Randolph, both of Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 790 days.

(21) Appl. No.: 08/530,684

(22) Filed: Sep. 18, 1995

(51) Int. Cl.$^7$ .................................................... C07C 7/17
(52) U.S. Cl. ..................... 585/857; 585/842; 208/223; 208/225; 208/280
(58) Field of Search .................................. 585/842, 857; 208/223, 225, 280

(56) References Cited

U.S. PATENT DOCUMENTS

| | | | |
|---|---|---|---|
| 3,929,924 | 12/1975 | Chapman | 260/683.42 |
| 3,957,628 | * 5/1976 | Siskin et al. | 208/223 |
| 4,371,731 | 2/1983 | Washer | 585/176 |
| 5,220,094 | 6/1993 | Eason | 585/716 |
| 5,284,993 | 2/1994 | Eastman | 585/842 |

* cited by examiner

Primary Examiner—Marian C. Knode
(74) Attorney, Agent, or Firm—Charles W. Stewart

(57) ABSTRACT

A process for removing sulfone from a liquid hydrocarbon containing a concentration of sulfone by mixing a liquid acid therewith and thereafter separating the resulting admixture into an acid phase and a hydrocarbon phase. The hydrocarbon phase has a concentration of sulfone less than such concentration in the liquid hydrocarbon.

11 Claims, 1 Drawing Sheet

METHOD FOR REMOVING SULFOLANE PRESENT IN HYDROCARBON

The present invention relates to the processing of an alkylation reactor effluent produced by the catalytic alkylation of olefins by isoparaffins using a hydrogen halide catalyst in a sulfone diluent. More particularly, the invention relates to the removal of sulfone from an alkylation reactor effluent.

BACKGROUND OF THE INVENTION

A recently discovered novel alkylation catalyst mixture contains a hydrogen halide component in a sulfone diluent. While the components of the alkylation catalyst mixture are substantially immiscible with hydrocarbons, particularly, an alkylate product, the sulfone component is still slightly soluble in hydrocarbon. Consequently, there can be a small concentration of sulfone in an alkylate product produced by the catalytic alkylation of olefins by isoparaffins using as the catalyst a hydrogen halide in a sulfone diluent. The concentration of sulfone in the alkylate product can range upwardly to about 4000 parts per million by weight (ppmw). A high concentration of sulfone in the alkylate product is undesirable because of the use of alkylate as a motor gasoline blending material. The concentration of sulfone in the alkylate should be less than about 100 ppmw.

SUMMARY OF THE INVENTION

Accordingly, an object of this invention is to provide a method for removing sulfone from an alkylation reactor effluent having an undesirably high concentration of sulfone so as to provide an alkylate product with a low concentration of sulfolane.

Thus, the inventive method provides for the removal of sulfone from a liquid hydrocarbon stream having a concentration of sulfone in the range of from about 150 ppmw to about 4000 ppmw. This method includes mixing within a mixing zone the liquid hydrocarbon stream with liquid hydrogen fluoride to form an admixture of hydrogen fluoride and the liquid hydrocarbon stream. The admixture is passed to a phase separation zone wherein it is separated into at least two liquid phases including a hydrocarbon phase and an acid phase. The hydrocarbon phase has a concentration of sulfone that is less than the concentration of sulfone in the liquid hydrocarbon stream, and the acid phase includes a concentration of sulfone.

Figure 1:
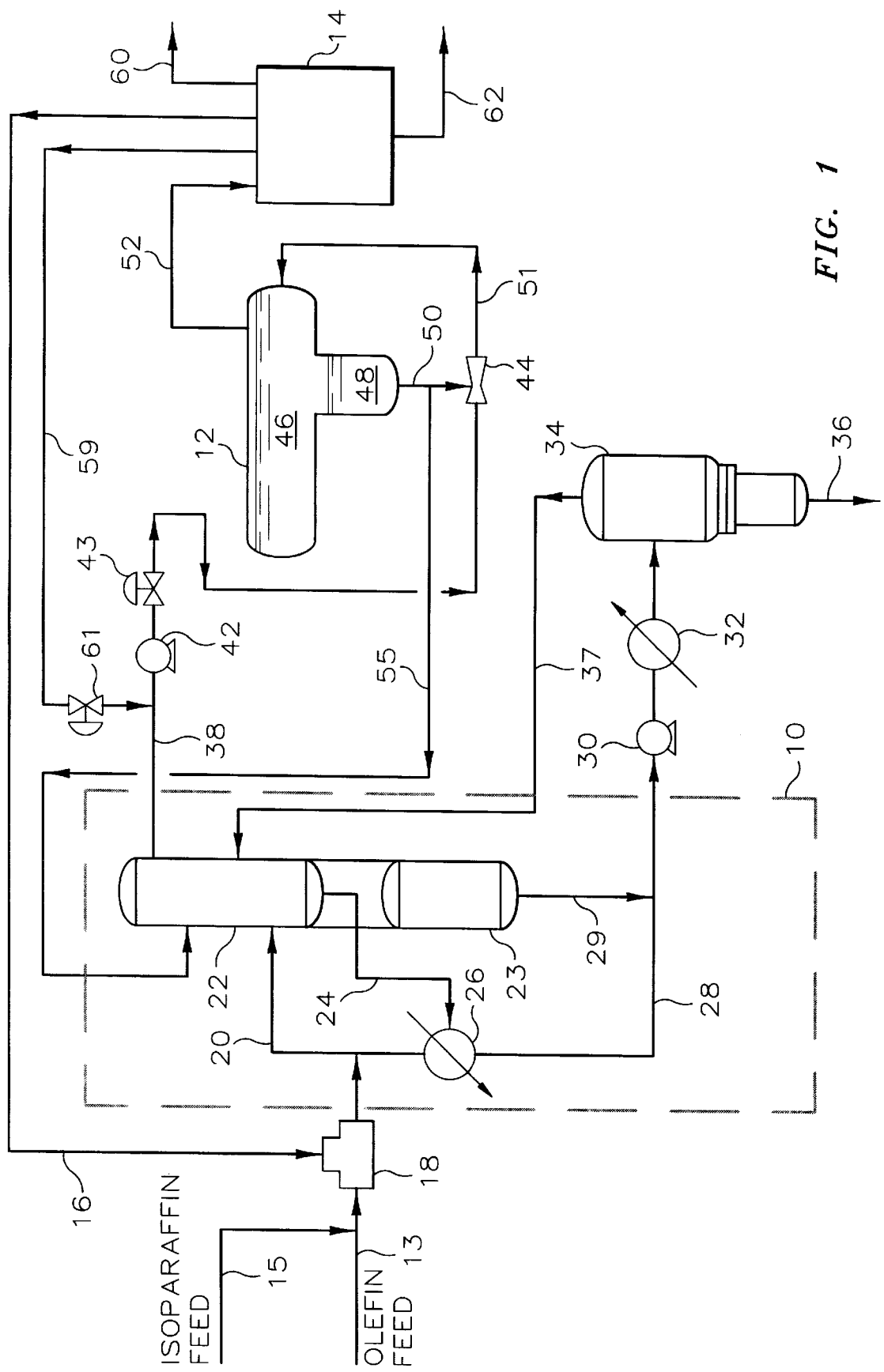
FIG. 1 is a schematic representation of the process which is one embodiment of the invention.

Other objects and advantages of the invention will be apparent from the following detailed description of the invention and the appended claims.

DETAILED DESCRIPTION OF THE INVENTION

The novel method described herein provides for the removal of contaminating concentration levels of sulfone contained in an alkylation reaction product known as alkylate. The alkylation reaction product, or alkylate, can have a concentration of the sulfone used as a diluent for a hydrogen halide component to form a novel alkylation catalyst mixture. Generally, the sulfone can be present in the alkylate up to its maximum solubility level therein. This concentration of sulfone, however, can be undesirable especially when the alkylate is used as a blending component of a gasoline end-product. Thus, it is necessary to remove a portion, preferably, a significant portion, of the concentration of sulfone contained in an alkylate product so as to provide a concentration of sulfone in the alkylate that is less than about 100 ppmw.

The alkylate product of the instant invention is a hydrocarbon produced by an alkylation process involving the catalytic alkylation of olefins with isoparaffins. Generally, alkylation processes contemplated in the present invention are those liquid phase processes wherein mono-olefin hydrocarbons such as propylene, butylenes, pentylenes, hexylenes, heptylenes, octylenes and the like are alkylated by isoparaffin hydrocarbons such as isobutane, isopentane, isohexane, isoheptane, isooctane and the like for production of high octane alkylate hydrocarbons boiling in the gasoline range and which are suitable for use in gasoline motor fuel. Preferably, isobutane is selected as the isoparaffin reactant and the olefin reactant is selected from propylene, butylenes, pentylenes and mixtures thereof for production of an alkylate hydrocarbon product comprising a major portion of highly branched, high octane value aliphatic hydrocarbons having at least seven carbon atoms and less than ten carbon atoms.

In order to improve selectivity of the alkylation reaction toward the production of the desirable highly branched aliphatic hydrocarbons having seven or more carbon atoms, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5 to about 20; and, most preferably, it shall range from 8 to 15. It is emphasized, however, that the above recited ranges for the molar ratio of isoparaffin-to-olefin are those which have been found to be commercially practical operating ranges; but, generally, the greater the isoparaffin-to-olefin ratio in an alkylation reaction, the better the resultant alkylate quality.

Isoparaffin and olefin reactant hydrocarbons normally employed in commercial alkylation processes are derived from refinery process streams and usually contain small amounts of impurities such as normal butane, propane, ethane and the like. Such impurities are undesirable in large concentrations as they dilute reactants in the reaction zone, thus decreasing reactor capacity available for the desired reactants and interfering with good contact of isoparaffin with olefin reactants. Additionally, in continuous alkylation processes wherein excess isoparaffin hydrocarbon is recovered from an alkylation reaction effluent and recycled for contact with additional olefin hydrocarbon, such nonreactive normal paraffin impurities tend to accumulate in the alkylation system. Consequently, process charge streams and/or recycle streams which contain substantial amounts of normal paraffin impurities are usually fractionated to remove such impurities and maintain their concentration at a low level, preferably less than about 5 volume percent, in the alkylation process.

Alkylation reaction temperatures within the contemplation of the present invention are in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 110° F.

Reaction pressures contemplated in the present invention may range from pressures sufficient to maintain reactants in the liquid phase to about twenty-five (25) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone, in the presence of the alkylation catalyst of the present invention generally should be sufficient to provide for essentially complete conversion of olefin reactant in the alkylation zone. Preferably, the contact time is in the range from about 0.05 minute to about 60 minutes. In the alkylation process of the present invention, employing isoparaffin-to-olefin molar ratios in the range of about 2:1 to about 25:1, wherein the alkylation reaction mixture comprises about 40–90 volume percent catalyst phase and about 60–10 volume percent hydrocarbon phase, and wherein good contact of olefin with isoparaffin is maintained in the reaction zone, essentially complete conversion of olefin may be obtained at olefin space velocities in the range of about 0.1 to about 200 volumes olefin per hour per volume catalyst (v/v/hr.). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.1 to about 200 (v/v/hr.) and allowing essentially complete conversion of olefin reactant in the alkylation zone.

The alkylation process may be carried out either as a batch or continuous type of operation, although it is preferred for economic reasons to carry out the process continuously. It has been generally established that in alkylation processes, the more intimate the contact between the feedstock and the catalyst the better the quality of alkylate product obtained. With this in mind, the present process, when operated as a batch operation, is characterized by the use of vigorous mechanical stirring or shaking of the reactants and catalyst.

In continuous operations, in one embodiment, reactants may be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and withdrawn from the reaction system while the partially spent catalyst is recycled to the reactor. If desired, a portion of the catalyst can be continuously regenerated or reactivated by any suitable treatment and returned to the alkylation reactor.

The alkylation catalyst used in the alkylation reaction can be a novel composition suitable for use as an alkylation catalyst which can comprise, consist of, or consist essentially of a hydrogen halide component and a sulfone component.

The hydrogen halide component of the catalyst composition or catalyst mixture can be selected from the group of compounds consisting of hydrogen fluoride (HF), hydrogen chloride (HCl), hydrogen bromide (HBr), and mixtures of two or more thereof. The preferred hydrogen halide component, however, is hydrogen fluoride, which can be utilized in the catalyst composition in anhydrous form, but, generally, the hydrogen fluoride component utilized can have a small amount of water. The amount of water present in the hydrogen fluoride and sulfolane mixture in no event can be more than about 30 weight percent of the total weight of the hydrogen fluoride component, which includes the water, and preferably, the amount of water present in the hydrogen fluoride component is less than about 10 weight percent. Most preferably, the amount of water present in the hydrogen fluoride component is less than 5 weight percent. When referring herein to the hydrogen halide component, or more specifically to the hydrogen fluoride component, of the catalyst composition of the invention, it should be understood that these terms mean either the hydrogen halide component as an anhydrous mixture or a mixture that includes water. The references herein to weight percent water contained in the hydrogen halide component means the ratio of the weight of water to the sum weight of the water and hydrogen halide multiplied by a factor of 100 to place the weight ratio in terms of percent.

The sulfones suitable for use in this invention are the sulfones of the general formula

wherein R and R' are monovalent hydrocarbon alkyl or aryl substituents, each containing from 1 to 8 carbon atoms. Examples of such substituents include dimethylsulfone, di n-propylsulfone, diphenylsulfone, ethylmethylsulfone and the alicyclic sulfones wherein the $SO_2$ group is bonded to a hydrocarbon ring. In such a case, R and R' are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the from of mixtures.

The alkylation reactor effluent contains an alkylate product produced by the alkylation process, which utilizes a sulfone and hydrogen halide catalyst at standard pressure and temperature conditions, and will generally be a liquid hydrocarbon having a concentration of sulfone in the range of from about 150 ppmw to about 4000 ppmw. More specifically, however, the sulfone concentration in the alkylation reactor effluent can be in the range of from about 150 ppmw to about 3000 ppmw and, most specifically, the concentration is in the range of from 200 to 2500 ppmw.

It is desirable to remove a portion, preferably a substantial portion, of the sulfone contained in the alkylation reactor effluent therefrom. This is accomplished by mixing with the alkylation reactor effluent a liquid acid comprising hydrogen fluoride but preferably containing a predominant amount of hydrogen fluoride to form an admixture of the alkylation reactor effluent and the liquid acid. The admixture is passed to a separation zone wherein the admixture is allowed to separate into at least two substantially immiscible liquid phases one of which is a hydrocarbon phase and the other is an acid phase. The hydrocarbon phase thus can have a concentration of sulfone that is less than the concentration of sulfone in the alkylation reactor effluent.

The liquid acid comprises hydrogen fluoride generally having a concentration of hydrogen fluoride exceeding about 80 weight percent. Preferably, the liquid acid will have a concentration of hydrogen fluoride of at least about 85 weight percent and, most preferably, the concentration is at least 90 weight percent. The concentration of hydrogen fluoride in the liquid acid can have an important impact on the performance of the method for removing sulfone from a liquid hydrocarbon containing such sulfone. The greater the hydrogen fluoride concentration, and thus the purity of the liquid acid, the better the extraction efficiency of the liquid acid.

The acid phase can have hydrogen fluoride present at the same concentration ranges as those of the liquid acid but further having a concentration of sulfone which has been removed from the alkylation reactor effluent. While the sulfone concentration in the acid phase is highly dependent upon the concentration of sulfone in the alkylation reactor effluent, it can generally be in the range upwardly to about 15 weight percent but, preferably, in the range of from about 0.1 weight percent to about 7.5 weight percent. Most preferably, the concentration of sulfone in the acid phase is in the range of from 0.1 weight percent to 5 weight percent.

The inventive method can provide for the removal of a significant portion of the concentration of sulfone in the alkylation reactor effluent. Particularly, at least about 40 weight percent of the concentration of sulfone in the alkylation reactor effluent is removed therefrom. Preferably, however, it is desirable to remove at least about 50 weight percent of sulfone from the alkylation reactor effluent; and, most preferably, at least 60 weight percent of the sulfone should be removed from the alkylation reactor effluent.

Regardless of the fractional amount of sulfone removed from the alkylation reactor effluent containing a concentration of sulfone, the aforementioned hydrocarbon phase having a concentration of sulfone less than the concentration of sulfone in the alkylation reactor effluent should have a concentration of sulfone less than about 100 ppmw. Preferably, the concentration of sulfone in the hydrocarbon phase is less than about 50 ppmw; and, most preferably, the concentration is less than 25 ppmw.

The mixing step can be performed by any means or method which suitably provides for mixing or contacting of the liquid acid with the alkylation reactor effluent to form an admixture. The subsequent separation of the admixture into at least two liquid phases can be performed by any means or method which suitably provides for its separation into the hydrocarbon phase and the acid phase.

When mixing or contacting the liquid acid with the alkylate, any apparatus suitable for providing intimate mixing or contact may be used such as flow or line mixers and mechanically agitated vessels. Examples of flow or line type mixers include eductors, jet mixers, injectors, orifices, mixing nozzles, valves, pumps, agitated line mixers, packed tubes, pipe lines and the like. The mechanically agitated vessels include such devices as vessels equipped with propellers or impellers utilized to accomplish mixing and dispersion.

It is generally desirable to use a continuous type process whereby liquid acid is continuously mixed with the alkylate followed by a phase separation of the resultant hydrocarbon phase and acid phase by any means or method which suitably provides for separating the at least two immiscible liquid phases including the hydrocarbon phase and acid phase. In the continuous process, it is common for the mixing or contacting step to be performed separately, and by a separate apparatus, from that of the separating step. Flow or line mixers provide suitable means for mixing in a continuous process. The mixing and phase separating steps can also be conducted in a batchwise fashion usually in a single vessel which defines both a mixing zone and a phase separation zone. Mechanically agitated vessels can be utilized as apparatus to permit the batchwise mixing of alkylation reactor effluent and liquid acid and separating of the resulting acid and hydrocarbon phases.

The preferred mixing means for mixing the liquid acid and alkylation reactor effluent to thereby form an admixture is an eductor utilized to withdraw from the separation zone the acid phase. The acid phase is, thus, used as the liquid acid.

As for the separation of immiscible liquid phases, a vessel, which defines a phase separation zone, can suitably be used; provided, it has the appropriate volume to permit the separation of the immiscible fluids by gravity or any other appropriate means. Other mechanical devices, such as, for example, centrifuges, can be used to perform the separation of the immiscible phases.

Any amount of liquid acid relative to the quantity of the alkylation reactor effluent can be utilized in the process provided that the amount of liquid acid mixed with the alkylation reactor effluent is sufficient for causing the subsequent formation of at least two immiscible, liquid phases including a hydrocarbon phase having a concentration of sulfone less than the concentration of sulfone in the alkylation reactor effluent, and an acid phase having a concentration of sulfone resulting from the removal of sulfone from the alkylation reactor effluent.

In the mixing step, a sufficient amount of liquid acid is to be mixed with the alkylation reactor effluent, containing sulfone, to subsequently provide a hydrocarbon phase containing a reduced concentration of sulfone. It is desirable to mix an amount of liquid acid with the alkylation reactor effluent such that the volumetric ratio of the liquid acid to the alkylation reactor effluent exceeds about 0.25:1 to thereby form the admixture. Generally, the volumetric ratio of liquid acid to alkylation reactor effluent can be in the range of from about 0.5:1 to about 2:1. Preferably, the volumetric ratio of liquid acid to alkylation reactor effluent can be in the range of from about 0.75:1 to about 1.5:1; and, most preferably, it is between 0.9:1 to 1.1:1.

The process conditions under which both the mixing and separation are performed include temperatures in the range of from about 0° F. to about 250° F., with 40° F. to 160° F. being preferred. The process pressures include those within the range of from about 0.5 atmospheres of absolute pressure to about 30 atmospheres of absolute pressure, with 0.95 atmospheres of absolute pressure to 25 atmospheres of absolute pressure being preferred.

Referring now to FIG. 1, the alkylation unit diagrammatically illustrated includes HF alkylation system 10, recontactor 12, and separation system 14 and other appertinent equipment. HF alkylation system 10 includes alkylation reactor 20, phase separator, or settler, 22, acid storage vessel 23, and acid cooler 26.

Olefin feed, isoparaffin feed, and recycle isoparaffin are charged to alkylation system 10 via conduits 13, 15 and 16, respectively, where they enter feed-recycle mixer 18 prior to being charged to alkylation reactor 20. The isoparaffin-olefin feed is contacted with an acid catalyst, containing hydrogen fluoride and a sulfone, in the reaction zone defined by alkylation reactor 20. From alkylation reactor 20, the effluent, which can contain hydrocarbon product (alkylate), acid catalyst, and other hydrocarbons, is introduced to settler 22 wherein an alkylation reactor effluent, containing alkylate and other hydrocarbons, is separated from the acid catalyst. Acid catalyst is removed from the bottom of settler 22 and flows through conduit 24 to heat exchanger 26 whereby it is cooled and, optionally, split. Part of the acid catalyst returns to alkylation reactor 20, and the rest may be conveyed through conduit 28 by pump 30, heated in heat exchanger 32, and then introduced to acid rerun vessel 34. The bottoms of acid rerun vessel 34 are removed through conduit 36 and treated to produce acid soluble oil (ASO) product. A regenerated acid catalyst is removed from the top of acid rerun vessel 34 and introduced into settler 22 via conduit 37, which is in fluid flow communication with acid rerun vessel 34 and settler 22. Additionally, makeup acid catalyst can be introduced from acid storage 23 into conduit 28 via conduit 29 when needed.

Alkylation reactor effluent is removed from alkylation system 10 via conduit 38 with the alkylation reactor effluent being pumped through conduit 38 and valve 43 by pump 42 into eductor 44. The flow of alkylation reactor effluent into eductor 44 is controlled by valve 43. Recontactor 12 defines a phase separation zone wherein two immiscible phases including a hydrocarbon phase 46 and an acid phase 48 are separated by gravity. The acid phase is drawn into eductor 44 via conduit 50 which provides for fluid flow communication between acid phase 48 and eductor 44. Eductor 44 defines a mixing zone and provides for mixing of the alkylation reactor effluent and acid phase to form an admixture. The admixture passes to recontactor 12 through conduit 51.

Within recontactor 12, a phase separation occurs whereby the hydrocarbon phase is formed having a concentration of sulfone less than the concentration of sulfone in the alkylation reactor effluent, and an acid phase is formed having a concentration of sulfone.

Conduit 52 is in fluid flow communication with both recontactor 12 and separation system 14. Recontactor effluent entering separation system 14 through conduit 52 is separated into products, including propane and lighter products, which are removed through conduit 60, and alkylate and n-butane products, which are removed through conduit 62. Isoparaffin is removed from the alkylate, recycled and returned to alkylation system 10 via conduit 16 where it is introduced to feed-recycle mixer 18. Hydrogen fluoride removed from the alkylate in separation system 14 flows into conduit 38 via conduit 59 and is returned as make-up hydrogen fluoride to recontactor 12 via conduit 38. Flow into conduit 38 is controlled by valve 61. Any accumulation of acid and alkylate impurities in recontactor 12 are purged by removal from recontactor 12 through conduit 50 into conduit 55 and passed to settler 22.

EXAMPLE I

Calculated

The information provided in Table 1 is a calculated material balance surrounding the mixer/eductor and phase separator of the process for removing sulfolane from an alkylation reactor effluent stream to thereby give a hydrocarbon stream having a reduced concentration of sulfolane. This Example demonstrates the beneficial reduction in sulfolane concentration achievable by recontacting hydrogen fluoride with an alkylation reactor effluent having a concentration of sulfolane to thereby remove at least a portion of the sulfolane. As can be observed from the information presented in Table 1, the sulfolane concentration in the alkylation reactor effluent is about 257 ppmw. A sulfolane removal rate of 92 percent is achieved. The sulfolane builds up in the acid phase to about 5 weight percent of the circulating acid. To control the sulfolane build up, the purge rate must be adjusted. Sulfolane recovery can be improved by increasing the hydrogen fluoride make up rate.

TABLE 1

Calculated Material Balance Around the Mixer-Recontactor System for Removing Sulfone from an Alkylation Reactor Effluent

| | Stream No. | | | | | |
|---|---|---|---|---|---|---|
| Stream Description | 38 Settler HC to Mixer | 61 Make-up Boot Acid to Mixer | Recontact Acid to Eductor | 51 Eductor Effluent | 52 Recont. Effl. To Processing | 55 Recontactor Purge to Settler |
| Components: lbs/hr | | | | | | |
| Ethane | 15.2 | 2.5 | 2.8 | 20.5 | 17.7 | 0.0 |
| Propane | 9,950.6 | 72.0 | 1,350.6 | 11,373.2 | 10,019.2 | 3.4 |
| Isobutane | 128,160.0 | 1.1 | 7,748.7 | 135,909.8 | 128,141.5 | 19.6 |
| N-Butane | 12,635.0 | 0.0 | 1,281.5 | 13,916.5 | 12,631.8 | 3.2 |
| Pentanes | 1,306.2 | 0.0 | 62.5 | 1,368.7 | 1,306.1 | 0.1 |
| C6+ (Alkylate) | 19,437.2 | 0.0 | 507.6 | 19,944.8 | 19,436.0 | 1.2 |
| HF | 924.2 | 900.0 | 286,750.0 | 288,574.2 | 1,100.7 | 723.5 |
| Sulfolane* | 44.7 | 0.0 | 16,330.0 | 16,374.7 | 3.3 | 41.4 |
| ASO | 1.8 | 0.0 | 685.3 | 687.1 | 0.0 | 1.8 |
| Totals - lbs/hr | 172,474.9 | 975.6 | 314,719.0 | 488,169.5 | 172,656.3 | 794.2 |
| *Sulfolane ppmw | 257 | | | | 19 | |

EXAMPLE II

This Example II gives the experimental procedure used to determine the ability of anhydrous HF to extract sulfolane from a hydrocarbon stream. The data show that in all cases greater than 70 percent of the sulfolane is removed from the hydrocarbon stream and, in most cases, the reduction is greater than 94 percent.

A continuous reactor system was constructed and used for the alkylation studies under continuous conditions. The reactor consisted of a 2' section of Monel schedule 40 pipe (308 mL) connected, via ¼" Monel tubing, to a Monel sight gauge (704 mL) used as a settling vessel. The reactor was charged with the desired amount of acid (typically 300 grams). The reactor was wrapped with ½" heating tape. The temperature of the acid phase was held at about 36–38° C. by a temperature controller attached to the heating tape and monitored by a thermocouple in the thermowell in the center of the reactor. The feed was blended with isobutane (about 90 parts by weight) and light alkylate (about 10 parts by weight). To this base feed was added sulfolane. The blended feed was then pumped into the reactor (about 180 g/hr) through an orifice to provide good dispersion of the hydrocarbon into the acid phase.

After passing through the static acid phase, the hydrocarbon effluent was sampled at the top of the reactor. The hydrocarbon sample was diluted with pure isooctane and the mixture analyzed for sulfur. A sample of the feed was pulled at the same time and treated in the same way. Table II gives the results for the sulfolane removal from the hydrocarbon phase.

TABLE II

Sulfolane Extraction from Hydrocarbon by HF Bench Riser Studies

| Feed Sulfolane, ppmw | 78 | 87 | 87 | 88 | 88 | 94 | 94 | 106 |
|---|---|---|---|---|---|---|---|---|
| Temperature, ° C. | 37.3 | 38.7 | 38.4 | 36.7 | 36.4 | 36.6 | 36.6 | 37.3 |
| Effluent Sulfolane, ppmw | 1 | 10 | 5 | 11 | 5 | 1 | 1 | 3 |
| % Reduction | 99 | 89 | 94 | 88 | 94 | 99 | 99 | 97 |
| Feed Sulfolane, ppmw | 106 | 112 | 126 | 126 | 188 | 188 | 533 | 533 |
| Temperature, ° C. | 37.3 | 38.9 | 37.0 | 38.1 | 36.6 | 36.6 | 37.1 | 36.7 |
| Effluent Sulfolane, ppmw | 3 | 34 | 2 | 1 | 41 | 6 | 32 | 2 |
| % Reduction | 97 | 70 | 98 | 99 | 78 | 97 | 94 | 100 |

Sulfolane Feed = Measured values from sample taken at appropriate time

EXAMPLE III

This Example III was performed in the same fashion as Example II, except the acid phase was comprised of 95% by weight HF and 5% by weight sulfolane. Table III summarizes the results for these experiments and shows that the efficiency of sulfolane removal is decreased by sulfolane build-up in the recontactor acid phase.

TABLE III

Sulfolane Extraction from Hydrocarbon by HF with 5% Sulfolane Bench Riser Studies

| Feed Sulfolane, ppmw | 117 | 261 | 261 | 277 | 277 |
|---|---|---|---|---|---|
| Temperature, ° C. | 37.9 | 36.8 | 38.3 | 37.4 | 38.9 |
| Effluent Sulfolane, ppmw | 87 | 175 | 181 | 98 | 156 |
| % Reduction | 26 | 33 | 31 | 65 | 44 |

While this invention has been described in terms of the presently preferred embodiment, reasonable variations and modifications are possible by those skilled in the art. Such variations and modifications are within the scope of the described invention and the appended claims.

That which is claimed:

1. A method for removing sulfone from a liquid hydrocarbon stream, said liquid hydrocarbon stream having a concentration of sulfone in the range of from about 150 ppmw to about 4000 ppmw, said method comprises the steps of:

mixing within a mixing zone said liquid hydrocarbon stream with a liquid acid, said liquid acid comprising HF, to form an admixture of said liquid hydrocarbon stream and said liquid acid;

passing said admixture to a phase separation zone wherein said admixture is separated into at least two liquid phases including a hydrocarbon phase, having a concentration of sulfone less than said concentration of sulfone in said liquid hydrocarbon stream, and an acid phase, having a concentration of sulfone.

2. A method as recited in claim 1, further comprising:
withdrawing said hydrocarbon phase from said separation zone.

3. A method as recited in claim 2, further comprising:
utilizing said acid phase as said liquid acid.

4. A method as recited in claim 3, wherein at least about 40 weight percent of said concentration of sulfone in said liquid hydrocarbon stream is removed therefrom to provide said concentration of sulfone less than said concentration of sulfone in said liquid hydrocarbon stream and said concentration of sulfone in said acid phase.

5. A method as recited in claim 4, wherein the weight ratio of said liquid acid to said liquid hydrocarbon stream is in the range of from about 0.5:1 to about 2:1.

6. A method as recited in claim 5 wherein said mixing zone is defined by an eductor utilized to withdraw from said separation zone said acid phase for use as recited in the utilizing step.

7. A method as recited in claim 6 wherein the sulfone is sulfolane.

8. A method as recited in claim 7 wherein the concentration of HF in said liquid acid exceeds about 80 weight percent.

9. A method as recited in claim 1 wherein the concentration of sulfone in said hydrocarbon phase is less than about 100 ppmw.

10. A method as recited in claim 1 wherein the concentration of sulfone in said acid phase is in the range upwardly to about 10 weight percent and the concentration of hydrogen fluoride in said acid phase exceeds about 80 weight percent.

11. A method as recited in claim 1 wherein the weight ratio of said liquid acid to said liquid hydrocarbon stream is in the range of from about 0.5:1 to about 5:1.

* * * * *